US012259366B2

United States Patent
Bathija et al.

(10) Patent No.: US 12,259,366 B2
(45) Date of Patent: Mar. 25, 2025

(54) CEMENT STRENGTH EVALUATION IN A SIMULATED DOWNHOLE SETTING WITH ACOUSTIC MEASUREMENTS

(71) Applicant: ARAMCO SERVICES COMPANY, Houston, TX (US)

(72) Inventors: Arpita P. Bathija, Houston, TX (US); Peter J. Boul, Houston, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 369 days.

(21) Appl. No.: 17/938,785

(22) Filed: Oct. 7, 2022

(65) Prior Publication Data

US 2024/0118181 A1   Apr. 11, 2024

(51) Int. Cl.
*G01N 3/24* (2006.01)
*G01N 29/07* (2006.01)
(Continued)

(52) U.S. Cl.
CPC .............. *G01N 3/24* (2013.01); *G01N 29/07* (2013.01); *G01N 29/14* (2013.01); *G01N 33/383* (2013.01); *G01N 2203/0025* (2013.01); *G01N 2291/01* (2013.01); *G01N 2291/0232* (2013.01); *G01N 2291/0289* (2013.01); *G01N 2291/106* (2013.01)

(58) Field of Classification Search
CPC .......... G01N 3/24; G01N 29/07; G01N 29/14; G01N 33/383; G01N 2203/0025; G01N 2291/01; G01N 2291/0232; G01N 2291/0289; G01N 2291/106; G01N 9/24; G01N 19/04
See application file for complete search history.

(56) References Cited

U.S. PATENT DOCUMENTS

| 6,612,156 B1 * | 9/2003 | Hakimuddin | B01F 31/85 73/597 |
| 2007/0056383 A1 * | 3/2007 | Deeg | G01N 33/383 73/788 |
| 2021/0302292 A1 | 9/2021 | Boul et al. | |

FOREIGN PATENT DOCUMENTS

| AU | 2009343308 B2 * | 12/2015 | ......... E21B 47/0005 |
| CA | 3114559 A1 * | 4/2019 | ............. E21B 34/06 |

(Continued)

OTHER PUBLICATIONS

Albawi, A., et al., "Experimental Set-Up for Testing Cement Sheath Integrity in Arctic Wells", OTC 24587, Offshore Technology Conference, Feb. 2014, pp. 1-11 (11 pages).

(Continued)

*Primary Examiner* — Francis C Gray
(74) *Attorney, Agent, or Firm* — Osha Bergman Watanabe & Burton LLP

(57) ABSTRACT

A cement bond test cell includes an outer cylinder and an inner cylinder coaxially disposed within the outer cylinder along a central axis. The inner cylinder defines an inner volume configured to be filled with a fluid. An annulus is formed between the outer cylinder and the inner cylinder and configured to be filled with a test cement. The cement bond test cell further includes an acoustic transmitter disposed within the inner volume and configured to be acoustically coupled to an interior surface of the inner cylinder by the fluid. The cement bond test cell further includes at least one acoustic receiver acoustically coupled to an exterior surface of the outer cylinder.

20 Claims, 8 Drawing Sheets

(51) Int. Cl.
*G01N 29/14* (2006.01)
*G01N 33/38* (2006.01)

(56) References Cited

FOREIGN PATENT DOCUMENTS

| CA | 3114546 C | * | 2/2022 | ............ E21B 21/08 |
|---|---|---|---|---|
| CN | 111827977 A | | 10/2020 | |
| KR | 101810724 B1 | * | 12/2017 | |

OTHER PUBLICATIONS

Kamali, Mohammadreza, et al., "Experimental Study of Hydraulic Sealability and Shear Bond Strength of Cementitious Barrier Materials", Journal of Energy Resources Technology, ASME, vol. 144, Feb. 2022, pp. 023007-1-023007-13 (13 pages).

Li, Juan, et al., "Deformation and damage of cement sheath in gas storage wells under cyclic loading", Energy Science & Engineering, Society of Chemical Industry and John Wyley & Sons Ltd., vol. 9, 2021, pp. 483-501 (19 pages).

Wang, Hua, "A cement bond evaluation method based on the full waveform from a monopole tool", SEG International Exposition and 87th Annual Meeting, SEG, 2017, pp. 875-879 (5 pages).

Wang, Hua, et al., "Understanding Acoustic Methods for Cement Bond Logging", The Journal of Acoustical Society of America, Acoustical Society of America, vol. 139, No. 5, May 2016, pp. 2407-2416 (10 pages).

Lamik, Abdelfattah, et al., "Evaluation of Cement-Casing & Cement-Rock Bond Integrity During Well Operations", SPE/ADC-202186-MS, SPE/IADC Middle East Drilling Technology Conference and Exhibition, May 2021, pp. 1-13 (13 pages).

\* cited by examiner

CEMENT STRENGTH EVALUATION IN A SIMULATED DOWNHOLE SETTING WITH ACOUSTIC MEASUREMENTS

BACKGROUND

In the oil and gas industry cementing is a fundamental process which enables drilling, completions, production, injection, and abandonment activities throughout the life of the well. During the cementing process, cement is injected (or pumped) into the annular space between the wellbore wall and a well casing string or in the annular space between two casing strings (or well liners). The cement is used to seal the annular space it fills and provide a barrier to fluid flow. The barrier created by the cement may be intended to keep unwanted fluids from entering or exiting the wellbore during drilling and throughout the life of the well. For example, the cement may keep fluids from a subsurface formation from entering the wellbore and traveling to another subsurface formation or to the surface. The cement also provides mechanical support to the wellbore walls throughout the drilling process and inhibits corrosion of the casing (and liners) that will remain after drilling is complete. Cement may also be used as one or more components of a plug used to seal a well during abandonment.

Cement shear bond strength measurement is a way to evaluate the bonding capability of the cement to the metal casing. If the cement bond is inadequate, it may result in leakage of one or more liquids from the producing or abandoned well. Cement debonding within oil and gas wells is a major cause of lost production and wellbore repair expenses. Therefore, reliable methods for experimentally assessing the shear bond strength of cement in a controlled laboratory setting are desired to improve the cement performance in the field before integrating them in or around a well.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments disclosed herein relate to a cement bond test cell for use in a test chamber. The cement bond test cell includes an outer cylinder and an inner cylinder coaxially disposed within the outer cylinder along a central axis. The inner cylinder defines an inner volume configured to be filled with a fluid. An annulus is formed between the outer cylinder and the inner cylinder and configured to be filled with a test cement. The cement bond test cell further includes an acoustic transmitter disposed within the inner volume and configured to be acoustically coupled to an interior surface of the inner cylinder by the fluid. The cement bond test cell further includes at least one acoustic receiver acoustically coupled to an exterior surface of the outer cylinder.

In another aspect, embodiments disclosed herein relate to a method. The method includes: installing a cement bond test cell into a test chamber configured to apply a stress in the cement bond test cell; filling an annulus between an outer cylinder and an inner cylinder of the cement bond test cell with a test cement; applying a stress to the cement bond test cell; emitting a plurality of acoustic signals from an acoustic transmitter disposed in a fluid filling the inner cylinder over a period of time; detecting each acoustic signal using an acoustic receiver acoustically coupled to an exterior surface of the outer cylinder over the period of time; determining a characteristic of each detected acoustic signal; detecting a commencement of a cement bond failure based, at least in part, on the characteristic of each of the detected acoustic signals; and determining a shear bond strength based, at least in part, on a measured axial stress at the commencement of the cement bond failure.

In yet another aspect, embodiments disclosed herein relate to a method. The method includes: installing a cement bond test cell into a test chamber configured to apply a stress in the cement bond test cell; filling an annulus between an outer cylinder and an inner cylinder of the cement bond test cell with a test cement; applying a stress to the cement bond test cell; emitting a plurality of acoustic signals from an acoustic transmitter disposed in a fluid filling the inner cylinder over a period of time; detecting each acoustic signal using an acoustic receiver acoustically coupled to an exterior surface of the outer cylinder over the period of time; determining a characteristic of each detected acoustic signal; and determining a density profile of the test cement at an instant in time based, at least in part, on the characteristic.

In still another aspect, embodiments disclosed herein relate to a system. The system includes a testing system including a test chamber configured to apply a stress in the test chamber and a cement bond test cell configured to be installed in the test chamber. The testing system is configured to apply a stress to the cement bond test cell. The cement bond test cell includes an outer cylinder and an inner cylinder coaxially disposed within the outer cylinder along a central axis. The inner cylinder defines an inner volume configured to be filled with a fluid. An annulus is formed between the outer cylinder and the inner cylinder and configured to be filled with a test cement. The cement bond test cell further includes an acoustic transmitter disposed within the inner volume and configured to be acoustically coupled to an interior surface of the inner cylinder by the fluid. The cement bond test cell further includes at least one acoustic receiver acoustically coupled to an exterior surface of the outer cylinder. The system further includes a computer processor configured to: control the stress applied by the testing system in the test chamber, activate the acoustic transmitter over a period of time, record an acoustic signal detected by the acoustic receiver over the period of time, determine a characteristic of the acoustic signal, determine a density profile of the test cement at an instant in time based, at least in part, on the characteristic, detect a commencement of a cement bond failure based, at least in part, on the characteristic of the acoustic signal detected by the acoustic receiver, and determine a shear bond strength based, at least in part, on a measured axial stress at the commencement of the cement bond failure.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn are not necessarily intended to convey any information regarding the actual shape of the particular elements and have been solely selected for ease of recognition in the drawing.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In the following description of FIGS. 1-9, any component described with regard to a figure, in various embodiments disclosed herein, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Thus, for example, reference to "a formation sample" includes reference to one or more of such samples.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowcharts may be omitted, repeated, and/or performed in a different order than the order shown. Accordingly, the scope disclosed herein should not be considered limited to the specific arrangement of steps shown in the flowcharts.

Figure 1:
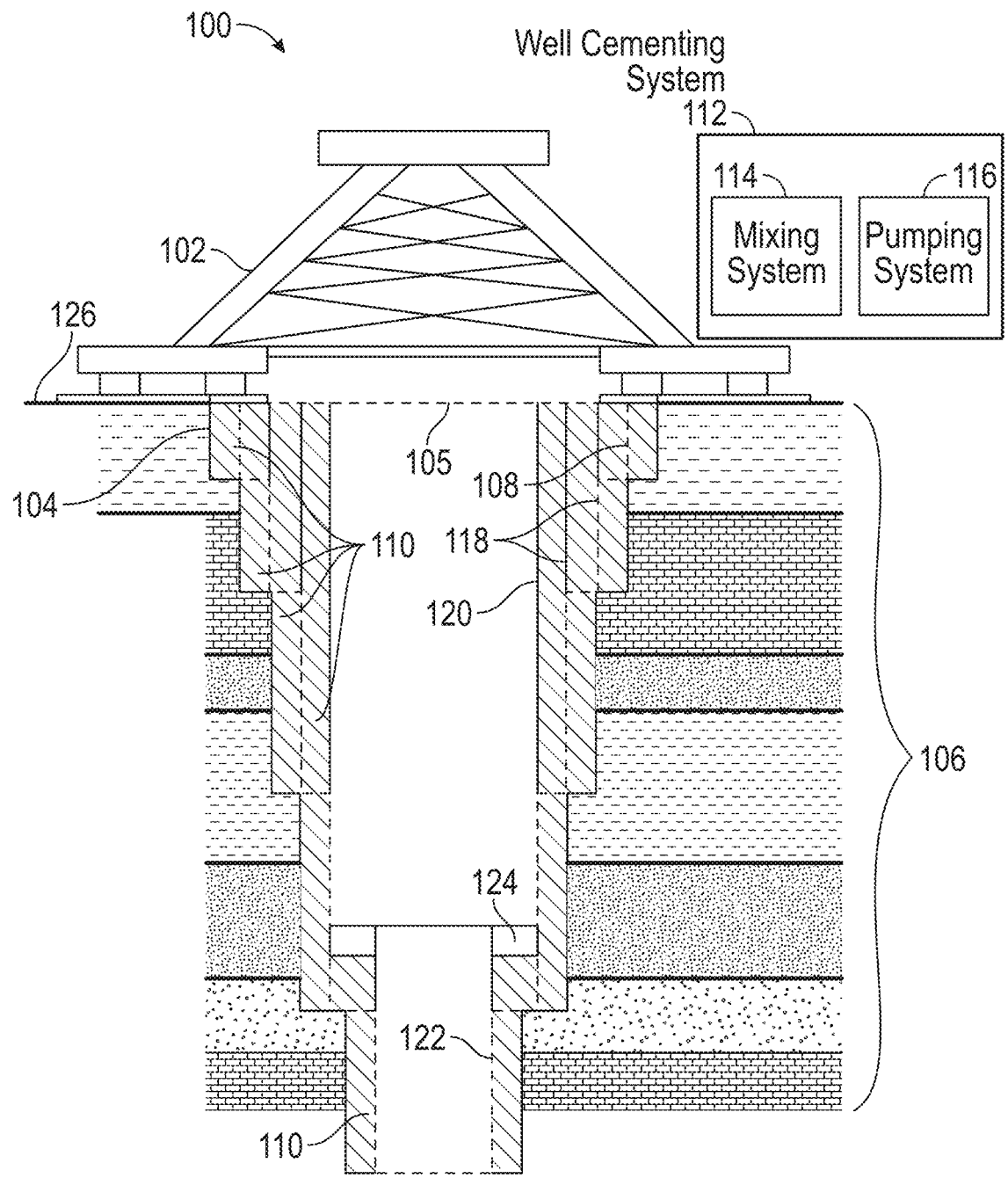
FIG. 1 illustrates a wellbore environment in accordance with one or more embodiments.

FIG. 1 illustrates a wellbore environment (100). The wellbore environment (100) includes a drill rig (102). The drill rig may be used to drill a wellbore (104) in sections of uniform diameter. Each section of the wellbore (104) is lined with a section of hollow metal pipe (or tubing) called a casing string (105). The casing string (105) is configured to fit inside the wellbore (104). The casing string (105) acts a barrier between subsurface layers (106) through which the wellbore (104) is drilled. The casing string (105) also provides mechanical structure and stability to the wellbore (104). The diameters of the sections of the wellbore (104) and the corresponding sections of casing string (105) decrease as the depth of the wellbore (104) increases. Typically, a first section of the casing string (105) is called the conductor casing string (108). After a first hole section is drilled the conductor casing string (108) is lowered into the wellbore (104). In so doing, an annular space is formed between the conductor casing string (108) and the wellbore (104). The annular space is filled with a cement (110) from a well cementing system (112). Once the conductor casing string (108) cement (110) is cured (i.e., the cement (110) has hardened) the next hole section may be drilled. An intermediate casing string (118) may be lowered through the conductor casing string (108) and into the open section of the wellbore (104). In so doing, an annular space is formed between the intermediate casing string (118) and the conductor casing string (108). Another annular space is also formed between the intermediate casing string (118) and the wellbore (104). Both annular spaces are filled with cement (110) by the well cementing system (112). There may be one or more intermediate casing strings (118) deployed in a single wellbore depending on well conditions. In the embodiment shown, two intermediate casing strings (118) are deployed. In this case, an annular space between the two intermediate casing strings (118) and an annular space between the inner intermediate casing string (118) and the wellbore (104) are also filled with cement (110). Once the intermediate casing string (118) cement (110) has cured, the next hole section may be drilled. A production casing string (120) may be lowered through the last intermediate casing string (118) and into the wellbore (104). In so doing, an annular space may be formed between the last intermediate casing string (118) and the production casing string (120). Another annular space may be formed between the production casing string (120) and the wellbore (104). Both annular spaces are filled with cement (110). A wellbore liner (122) may be used in the last hole section. The wellbore liner (122) may be lowered through the production casing string (120) and into the wellbore (104) on to a wellbore liner hanger (124). In so doing an annular space is formed between the production casing string (120), the wellbore liner (122), and the wellbore liner hanger (124). Another annular space is also formed between the wellbore liner (122) and the wellbore (104). Both annular spaces are filled with cement (110) by the well cementing system (112).

Continuing with FIG. 1, the well cementing system may include components such as a cement mixing system (114) and a cement pumping system (116). The cement mixing system (114) may include holding tanks for liquids and solids, mixers, pumps, and other components required to mix the cement (110) according to a cement plan. The cement pumping system (116) may include holding tanks for cement (110) and other fluids, as well as pumps, and plugs used to control the flow of the cement (110) into the annular spaces.

A person of ordinary skill in the art will recognize that the number of the wellbore (104) sections and the number of the casing string (105) sections used in drilling a well will depend on the wellbore path (position and trajectory) through subsurface layers (106) and other factors such as the anticipated overburden pressure, pore pressure, and fracture gradient of the subsurface layers (106) through which the wellbore (104) is to be drilled. It may also be recognized by a person of ordinary skill in the art that the cement (110) used to fill each of the annular spaces formed between sections of the casing string (105) and between sections of the casing string (105) and the wellbore (104) may or may not fill the annular space all the way to the surface (126) as shown. Further, a person of ordinary skill in the art may also recognize that the cement (110) used may vary in composition in each hole section or within a section.

Cement shear bond strength and settling density are two characteristics of a cement (110) that may be used to determine the suitability of a cement (110) to be used for a given purpose. For example, the cement characteristics may be used to determine if a cement (110) is suitable to be used in cementing casing sections into a wellbore (104) in a wellbore environment (100). Cement characteristics may depend on the cement mixture composition and properties. Cement characteristics may also depend on the environmental factors to which the cement (110) is exposed to during the period of time. The period of time includes from the time the cement (110) is mixed, pumped, cured, and aged in the wellbore (104). Some of the environmental factors may include casing pressure, pore pressure, loading pressure, and temperature. These factors, among others such as the wellbore (104) utilization, material availability, and casing/liner compatibility may be taken into consideration when designing a cementing program.

Currently, a push-out test may be performed to assess the shear bond strength of cement. Typically, the push-out test may be conducted in a laboratory setting. at standard temperature and pressure (e.g., room temperature and atmospheric pressure). Similarly, a settling density profile may be developed in a laboratory setting at standard temperature and pressure conditions. Current methods to produce the settling density profile require destructive testing of the cement sample. Further, the current method of producing the settling density profile is labor and time intensive. The current method generally requires a cement sample to be manually broken into small pieces and catalogued according to their location in the cement sample before being dried and weighed. An apparatus and a method of using the same are disclosed herein. The apparatus and the method may be utilized to determine cement characteristics such as the cement shear bond strength and the settling density of a cement mixture at downhole conditions (i.e., at temperatures and pressures that might be encountered in the wellbore (104)) in a laboratory setting. In some embodiments the apparatus and method may be used to determine the effect of casing (or liner) materials and surface finishes on cement bond strength (or other cement characteristics) instead of, or in addition to, testing the cement mixture. Further, the apparatus and methodology allow the settling density profile to be produced simultaneously with the cement curing process without the need for additional manual testing.

Figure 2:
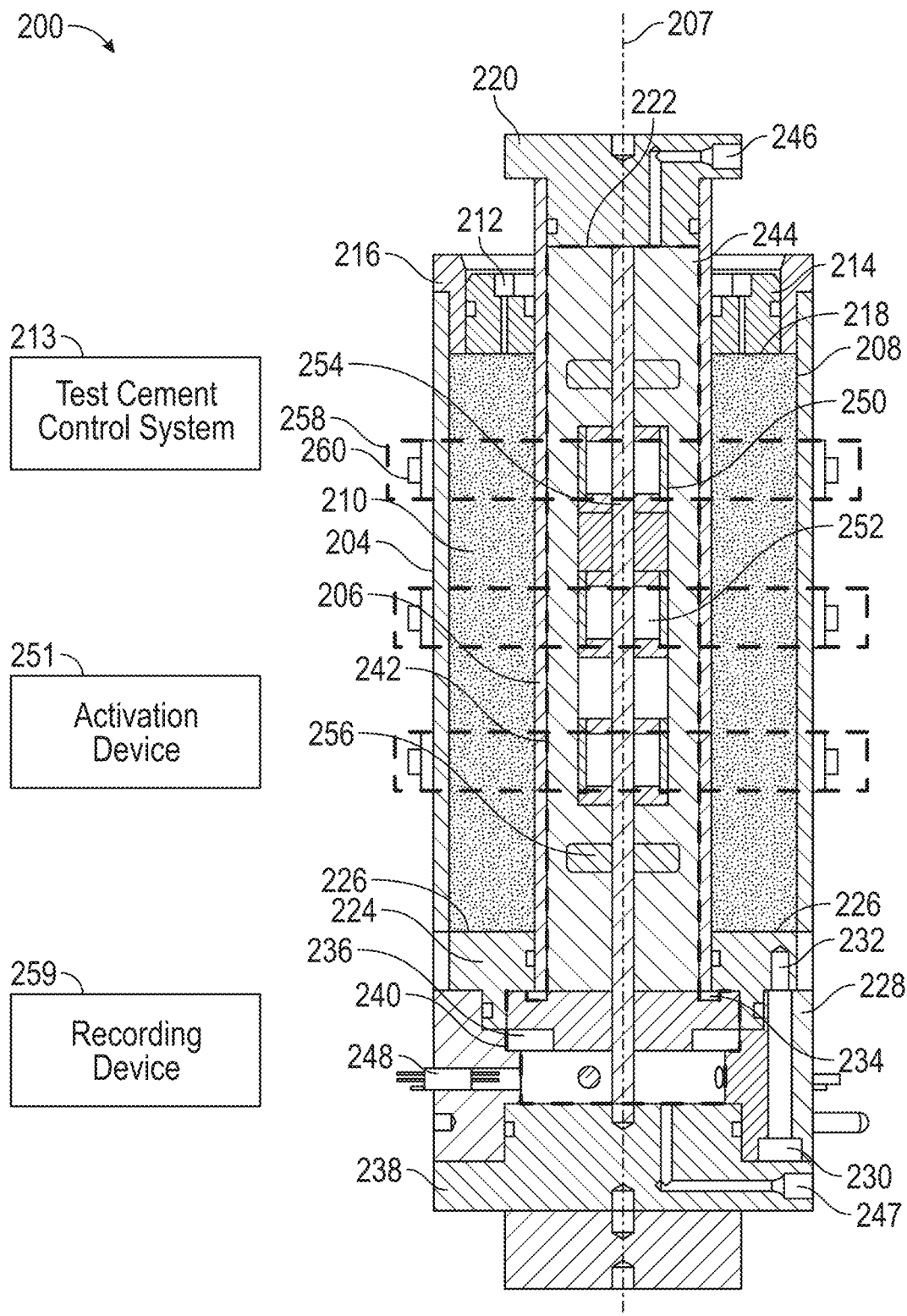
FIG. 2 depicts a cement bond test cell in accordance with one or more embodiments.

In accordance with one or more embodiments, FIG. 2 provides a drawing of a cement bond test cell (200). The cement bond test cell (200) includes an outer cylinder (204) and an inner cylinder (206). The outer cylinder (204) and the inner cylinder (206) may be coaxially disposed on a central axis (207). The disposition of the inner cylinder (206) inside the outer cylinder (204) forms an annulus (208) between the outer cylinder (204) and the inner cylinder (206). A pressure equalization piston (214) is shaped to fit inside a space between a top receiver (216) and the inner cylinder (206). The top receiver (216) is shaped to fit in the space between the pressure equalization piston (214) and the outer cylinder (204). The top receiver (216) is further shaped to contact the top of the outer cylinder (204). Together the pressure equalization piston (214), the top receiver (216), the outer cylinder (204) and the inner cylinder (206) form an annulus top seal (218). A top plug (220) is shaped to fit inside and contact the inner cylinder (206). Together the top plug (220) and the inner cylinder (206) form an inner cylinder top seal (222). An adapter (224) is shaped to fit in between the outer cylinder (204) and the inner cylinder (206). Together the adapter (224), the outer cylinder (204) and the inner cylinder (206) form an annulus bottom seal (226). The adapter is further shaped to fit inside a connection chamber (228). The connection chamber (228) is shaped to receive the adapter and contact the outer cylinder (204). The connection chamber (228) may also have a plurality of counterbored mounting through holes (230). The counterbored mounting through holes (230) are shaped to receive a mounting device, such as a bolt, that may be threaded into a tapped mounting hole (232) in the adapter (224). The connection chamber (228) may further be shaped to receive a stop ring (234) and a catch ring (236). The stop ring (234) may be mounted to the inner cylinder (206). The catch ring (236) may be mounted or placed inside the connection chamber (228). The catch ring (236) has an inside diameter that is smaller than the inside diameter of the stop ring (234). A base (238) is shaped to receive the connection chamber (228). Together the base (238), the connection chamber (228), the adapter (224), and the inner cylinder (206) form an inner cylinder bottom seal (240).

A person of ordinary skill in the art will recognize that the inner cylinder (206) may simulate a section of the casing string (105) inside a wellbore (104). The outer cylinder may simulate another section of casing string (105) or the subsurface layers (106).

Continuing with FIG. 2, the annulus (208) is configured to be filled with a test cement (210). The test cement (210) may be introduced to the annulus through a test cement channel (212). The test cement channel (212) may be connected to a test cement control system (213). The test cement control system (213) may include components such as a test cement reservoir, mixers, pumps, sensors, and one or more computers configured to mix and pump the test cement (210) into the annulus (208) of the cement bond test cell (200). In some embodiments the test cement channel (212) may be located in the pressure equalization piston (214). In other embodiments the test cement channel (212) may be located elsewhere, such as in the outer cylinder (204) or in the connection chamber (228) or adapter (224).

Still continuing with FIG. 2, an inner volume (242) is formed by the inner cylinder (206), the inner cylinder top seal (222) and the inner cylinder bottom seal (240). The inner volume (242) is configured to be filled with a fluid (244). In some embodiments the fluid (244) may be introduced to the inner volume (242) through an inner volume fluid inlet (246). In other embodiments the inner volume fluid inlet (246) may be located elsewhere such as in the base (238) or in the connection chamber (228). In some embodiments the inner volume fluid inlet (246) may be used to pressurize the inner volume (242). In other embodiments there may be an inner volume fluid pressure channel (247).

A person of ordinary skill in the art will recognize that components described may have variation and may not be fully described for the sake of brevity. For instance, the top receiver (216) and the pressure equalization piston (214) may be considered one piece; the base (238) may have greater diameter than the connection chamber (228); the annulus top seal (218), the annulus bottom seal (226), the inner cylinder top seal (222), and the inner cylinder bottom seal (240) may include components not described such as O-rings or other gaskets that are intended to assist in creating a seal.

Again, continuing with FIG. 2, an electrical feedthrough (248) may be disposed in the connection chamber (228). The electrical feedthrough (248) is configured to allow electrical communication between an electrical device disposed in the inner volume (242) of the cement bond test cell (200) and an activation device (251) outside of the cement bond test cell (200). The electrical device may be an acoustic transmitter (250). The acoustic transmitter (250) may be coupled to the interior surface of the inner cylinder (206) by the fluid (244). The acoustic transmitter (250) may include a plurality of acoustic sources (252). The acoustic sources (252) may be capable of operating independently or as a group. The acoustic sources (252) may be piezoelectric crystals. Further, the acoustic sources (252) may be affixed to an acoustic support structure (254) that is disposed along the central axis (207). The acoustic sources (252) may be placed at intervals along the central axis (207). In so doing, each of the acoustic sources will have an axial elevation. In some embodiments the acoustic support structure (254) may be composed of a rigid material such as a metal bar. In other embodiments the acoustic support structure (254) may be composed of a flexible material such as a metal or plastic wire. In some embodiments the acoustic support structure (254) may include at least one acoustic support centralizer (256). In some embodiments the acoustic support structure (254) may be connected to the base (238). In other embodiments the acoustic support structure may be connected to the top plug (220). In still other embodiments the acoustic support structure may be connected to both the top plug (220) and the base (238).

Still continuing with FIG. 2, at least one acoustic receiver (258) may be coupled to the exterior of the outer cylinder (204). The acoustic receiver (258) may include or be connected to a recording device (259). In some embodiments, the acoustic receiver (258) may be acoustically coupled using an adhesive compound, such as epoxy. In other embodiments the acoustic receiver (258) may be temporarily or permanently affixed by physical connectors (e.g., a bolt) or welded in place. The acoustic receiver (258) may include a plurality of acoustic detectors (260). The plurality of acoustic detectors (260) may form a coplanar acoustic detector array. Each of the plurality of acoustic detectors (260) may be disposed at an azimuthal interval around a circumference of the outer cylinder (204). A plane of the of the coplanar acoustic detector array may be perpendicular to the central axis (207) of the inner cylinder (206). The coplanar acoustic detector array may be placed at an elevation coincident with the axial elevation of each of the acoustic sources (252).

By way of example, in one embodiment, the at least one acoustic receiver (258) may include, for example, three acoustic receivers. The number of acoustic receivers may be equal to the number of acoustic sources (252). Each acoustic receiver (258) may include four acoustic detectors. The four acoustic detectors of each acoustic receiver (258) would form a coplanar acoustic detector array. Thus, there would be three acoustic detector arrays each having four acoustic detectors. Each of the acoustic detectors (260) within the coplanar acoustic detector array may be placed at an azimuthal interval of 90 degrees around the circumference of the outside cylinder. The acoustic detectors (260) would then have an azimuthal position of 0, 90, 180, and 270 degrees respectively. The plane of the coplanar acoustic detector array may be perpendicular to the central axis (207) of the inner cylinder (206). Finally, the plane of the coplanar acoustic detectors may be placed at the axial elevation coincident with each of the acoustic sources (252). In this example the total number of acoustic detectors (260) would be twelve.

In some embodiments the acoustic transmitter (250) may be configured with fewer or greater numbers of acoustic sources (252). In some embodiments, the least one acoustic receiver may include any greater number of acoustic receivers. Likewise, the acoustic receiver (258) may include any number of acoustic detectors (260). Further, the acoustic detectors (260) and the acoustic sources (252) can be placed in a variety of relative positions to one another. For example some of the variety of relative positions may include: the plane of the acoustic detectors (260) could be tilted such that the plane of acoustic detectors (260) is not perpendicular to the central axis (207), irregular azimuthal intervals of the acoustic detectors (260) could be chosen, unequal numbers of acoustic detectors (260) could be chosen for each acoustic receiver (258), irregular axial elevation intervals could be selected for the acoustic sources (252), the alignment of acoustic detectors (260) of each acoustic receiver (258) may not be vertical, and other such variety. A person of ordinary skill in the art will recognize that obtaining a geometric relationship (distances, angles, orientations, etc.) between the acoustic sources (252) and the acoustic detectors (260) is of importance in processing a data set acquired using the described apparatus.

Figure 3:
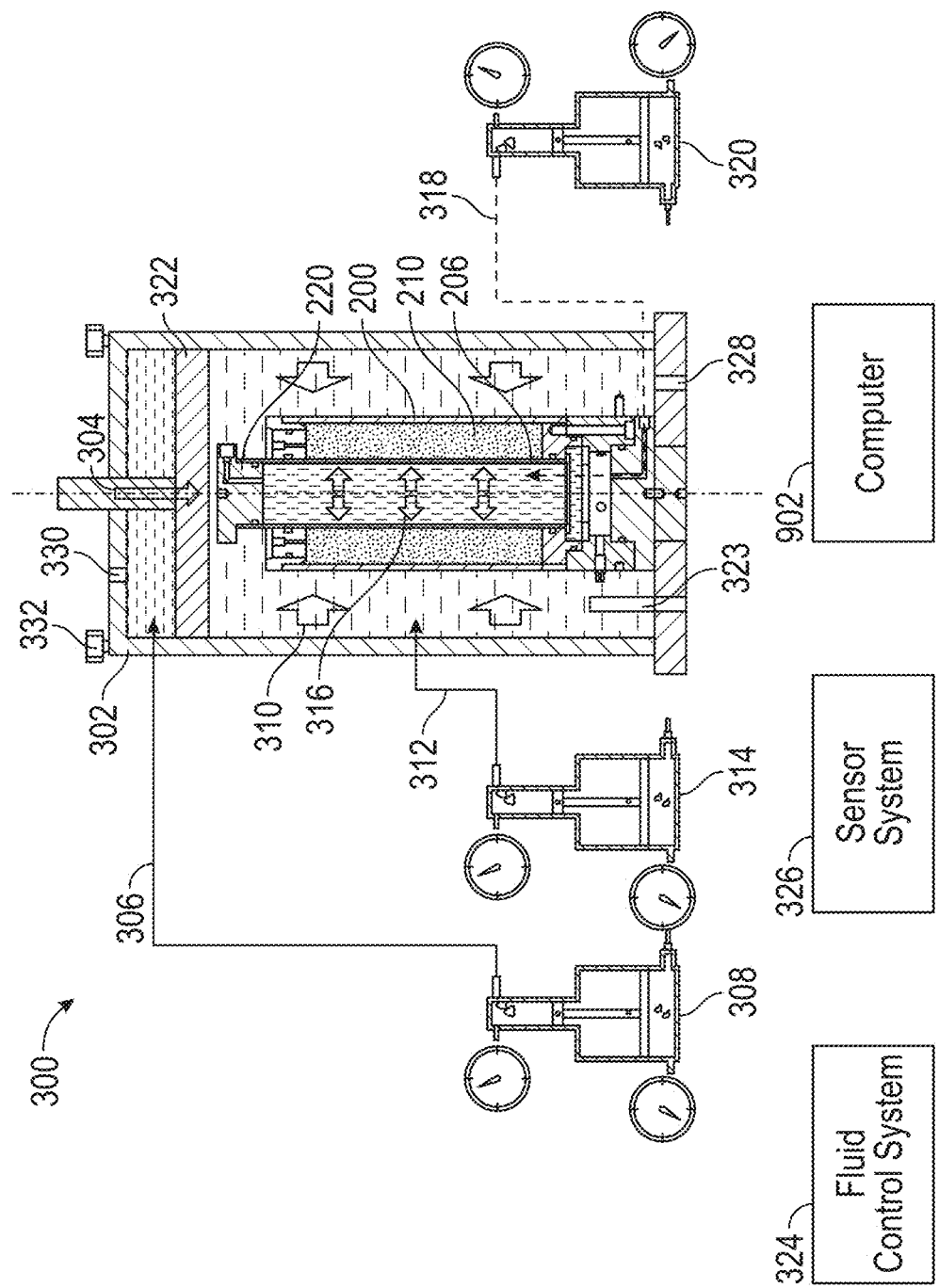
FIG. 3 depicts a test system in accordance with one or more embodiments.

FIG. 3 shows the cement bond test cell (200) installed into a test chamber (302). In accordance with one or more embodiments the test chamber (302) may be a component of a testing system (300). The testing system (300) may be a tri-axial test system. The testing system (300) may be configured to apply at least one stress in the test chamber (302). An axial stress (304) may be induced in the test chamber (302) through an axial pressure line (306). The axial pressure line (306) may be connected to an axial pressure generator (308). The axial stress (304) may be transferred to the cement bond test cell (200) by contact of a loading piston (322) with the top plug (220) of the cement bond test cell (200). The axial stress (304) is further transferred from the top plug (220) to the inner cylinder (206). A horizontal stress (310) may be induced in the test chamber (302) through a horizontal pressure line (312). The horizontal pressure line (312) may be connected to a horizontal pressure generator (314). Similarly, a radial stress (316) may be induced in the inner volume (242) through a radial pressure line (318) that passes through the inner volume fluid pressure channel (247). The radial pressure line (318) may be connected to a radial pressure generator (320).

The radial stress (316) may simulate a casing pressure inside a wellbore (104). The horizontal stress (310) may simulate a confining pressure (or pore pressure) of the subsurface layers (106) that may act on a wellbore (104) or the casing string within the wellbore (104). The axial stress (304) may simulate a vertical loading weight that may act on the casing string in wellbore (104).

Continuing with FIG. 3, the testing system (300) may include a heating element (323). The heating element (323) may be capable of heating the test chamber (302) to simulate a temperature that may be encountered in a wellbore (104).

Still continuing with FIG. 3, the testing system (300) may include a fluid control system (324) that may be used to operate any and all of the axial pressure generator (308), the horizontal pressure generator (314), the radial pressure generator (320). The fluid control system (324) may also be used to control the filling of the inner volume (242) with the fluid (244). The testing system (300) may also include a sensor system (326) which may include sensors (such as pressure gauges, strain meters, and temperature probes to measure and monitor any and all of the axial stress (304), the horizontal stress (310), and the radial stress (316) and any other operating parameters or features of the testing system (300). The test chamber (302) may also include at least one test chamber electrical feedthrough (328). The test chamber electrical feedthrough (328) may allow an electrical connection between instruments such as the heating element (323) and the acoustic receiver (258), acoustic transmitter (250) to be connected to systems and devices outside of the test chamber such as the fluid control system (324), the sensor system (326), the activation device (251), and the recording device (259).

Still continuing with FIG. 3, the testing system (300) may also include components such as a pressure relief valve (330) and mounting devices (332) that enable the test chamber to manage pressures/stresses that may be present in the test chamber (302) during testing.

One of ordinary skill in the part may recognize that a testing system (300) with a test chamber (302) may have the capability to simulate many conditions that may be encountered in a wellbore (104). One of ordinary skill in the art may also recognize that it may not be necessary to simulate all of the conditions that a wellbore (104) may encounter. As such, in some embodiments, the cement bond test cell may be installed in an alternate test system such as a load frame with a hydraulic press or screw configured to apply only the axial stress (304).

Figure 4:
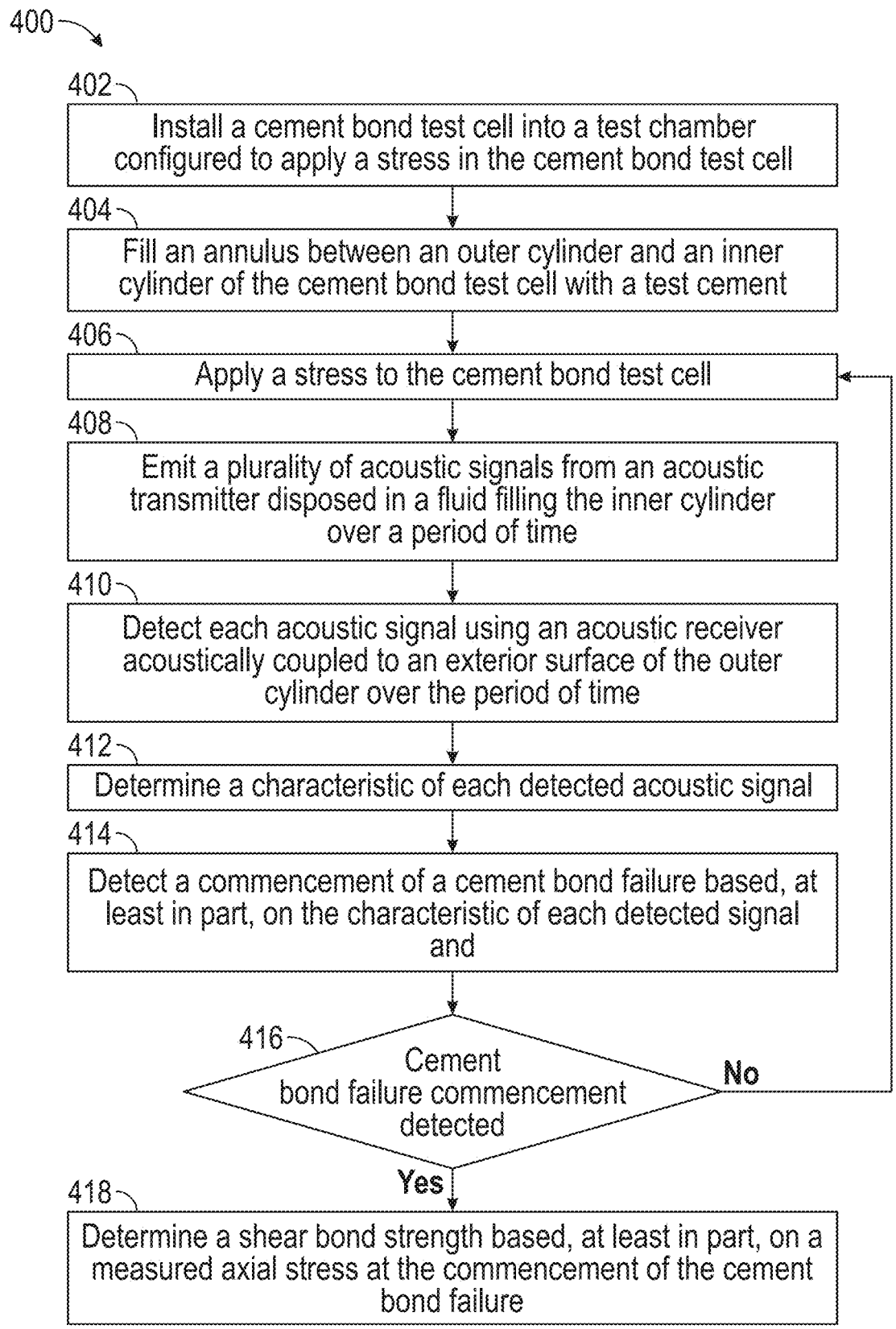
FIG. 4 depicts a flowchart in accordance with one or more embodiments.

In accordance with one or more embodiments, FIG. 4 provides a flowchart (400) describing the method of using the cement bond test cell (200) to determine a cement shear bond strength at simulated downhole conditions. Testing under simulated wellbore conditions may provide more reliable or more realistic results than tests, such as the push-out tests currently used by those of ordinary skill in the art.

In Step 402 the cement bond test cell apparatus may be installed in a test chamber. The test chamber (302) may be a component of a testing system (300). The testing system (300) may be a tri-axial testing system configured to apply a stress to the cement bond test cell (200).

In Step 404 the annulus (208), i.e., the space between the outer cylinder (204) and inner cylinder (206), of the cement bond test cell (200) is filled with a test cement. In some implementations Step 404 may be completed prior to Step 402.

In Step 406 a stress may be applied to the cement bond test cell (200) using the testing system (300). The stress may include the axial stress (304), the horizontal stress (310), or the radial stress (316) the testing system (300) is capable of generating. The testing system (300) may also subject the cement bond test cell (200) to heat which may simulate a wellbore temperature. A person of ordinary skill in the art may recognize that applying only the axial stress, and no heat, may be similar to the method of conducting a typical push-out test.

In Step 408 a plurality of acoustic signals may be emitted from an acoustic transmitter (250) disposed in a fluid filling the inner volume (242) of the inner cylinder (206) over a period of time. Each of the acoustic signals may be controlled, at least in part, by the activation device (251). The activation device (251) may control parameters such as stop, start, interval timing, relative timing between acoustic sources (252), frequency, etc. The acoustic signals may be emitted continuously or intermittently over a period of time. The period of time may be a duration that includes the test cement curing time and the loading process (i.e., the application of the axial stress (304) to the cement bond test cell).

In Step 410 each acoustic signals emitted in Step 408 may be detected by an acoustic receiver (258) acoustically coupled to the exterior surface of the outer cylinder (204). One of ordinary skill in the art will recognize that the acoustic receiver (258) may record acoustic signals that are generated by other acoustic generators (such as micropore or fracture closure or opening or other events that may generate acoustic signal or vibration).

In Step 412 a characteristic of each detected acoustic signal may be determined. Characteristics of the detected acoustic signal may be acoustic travel (arrival) time and acoustic amplitude.

In Step 414 a commencement of a cement bond failure may be detected based, at least in part, on the characteristic of each of the detected acoustic signals. If the commencement of the cement bond failure is not detected at a decision node (416) the method recycles back to Step 406 and repeats. If the commencement of the cement bond failure is detected at the decision node (416) the method proceeds to the next step.

In Step 418 a shear bond strength can be determined based, at least in part, on the measured axial stress (304) at the commencement of the cement bond failure.

In one or more embodiments, the commencement of the cement bond failure may correspond to a weakening of the cement strength, which is analogous to a change in the characteristic of the detected acoustic signals. For example, the weakening of the cement strength is analogous to increase of acoustic arrive time or decrease of acoustic amplitude. In some embodiments, the commencement of the cement bond failure may be detected based, at least in part, on an increase of acoustic arrive time or a decrease of acoustic amplitude.

Additionally or alternatively, the commencement of cement shear bond failure may be detected by observing a displacement of the inner cylinder (206) relative to a reference point, for example the outer cylinder (204). The maximum shear bond strength may then be determined by dividing the loading stress at the time of shear bond failure by the area of the cement surface, i.e., $\Gamma=F/A$, where $\Gamma$ is the shear bond strength, F is the loading force in kN, and A is the surface area of the cement-inner cylinder interface. The surface area A can be determined by the equation $A=2\pi rh$, where r is the outer radius of the inner cylinder and h is the length of the cement column.

The acoustically based detection of cement bond failure may result in a lower shear bond strength because the commencement of the cement bond failure may occur before the displacement of the inner cylinder (206) is observed. Having an estimate of the shear bond strength (acoustically based) and the maximum shear bond strength (displacement based) may lead to more reliable cement mixture for use in a wellbore environment (100).

Figure 5:
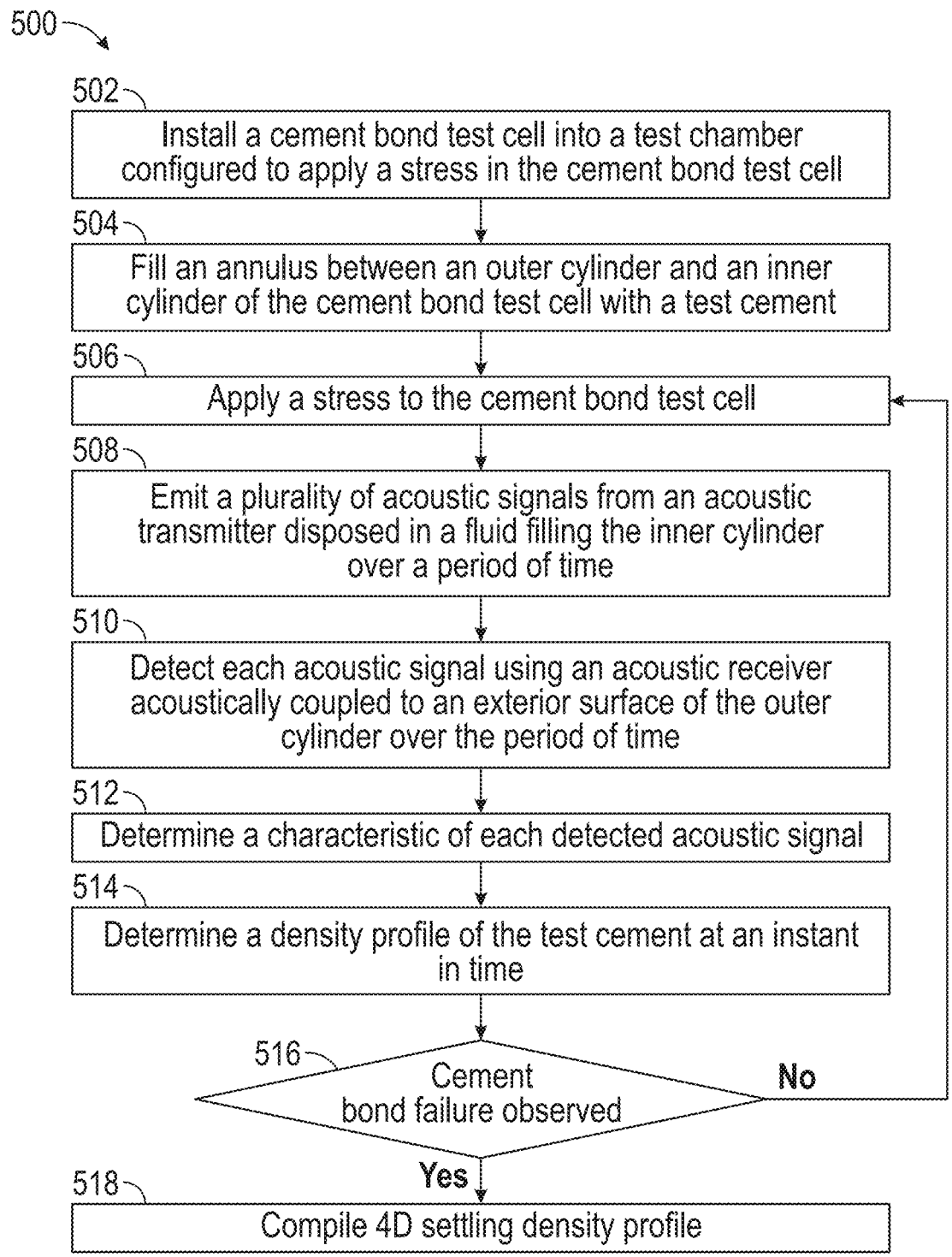
FIG. 5 depicts a flowchart in accordance with one or more embodiments.

In accordance with one or more embodiments, FIG. 5 provides a flowchart (500) describing the method of using the cement bond test cell (200) to determine a settling density profile of a test cement. In some embodiments the method of determining a settling density profile may be conducted simultaneously with the determination of the cement shear bond strength.

In Step 502 the cement bond test cell apparatus may be installed in a test chamber. The test chamber (302) may be a component of a testing system (300). The testing system (300) may be a tri-axial testing system configured to apply the stress to the cement bond test cell (200).

In Step 504 the annulus (208), i.e., the space between the outer cylinder (204) and inner cylinder (206), of the cement bond test cell (200) is filled with a test cement. In some implementations Step 504 may be completed prior to Step 502.

In Step 506 a stress may be applied to the cement bond test cell (200) using the testing system (300). The stress may include the axial stress (304), the horizontal stress (310), or the radial stress (316) the test system (300) is capable of generating. The testing system (300) may also subject the cement bond test cell (200) to heat which may simulate a wellbore temperature. A person of ordinary skill in the art may recognize that it is not necessary to apply any of the stresses to the cement bond test cell to carry out the determination of the settling density profile. That is, the method of determining the settling density profile may be performed under a condition that is selected for the determination of the cement shear bond strength. The condition may also be selected to replicate the typical method of determining the settling density profile at standard temperature and pressure.

In Step 508 a plurality of acoustic signals may be emitted from an acoustic transmitter (250) disposed in a fluid filling the inner volume (242) of the inner cylinder (206) over a period of time. Each of the acoustic signals may be controlled, at least in part, by the activation device (251). The activation device (251) may control parameters such as stop, start, interval timing, relative timing between acoustic sources (252), frequency, etc. The acoustic signals may be emitted continuously or intermittently over a period of time that may include the test cement curing time and the loading process (i.e., the application of the axial stress (304) to the cement bond test cell).

In Step 510 each acoustic signals emitted in Step 508 may be detected by an acoustic receiver (258) acoustically coupled to the exterior surface of the outer cylinder (204). One of ordinary skill in the art will recognize that the acoustic receiver (258) may record acoustic signals that are generated by other acoustic generators (such as micropore or fracture closure or opening or other events that may generate acoustic signal or vibration).

In Step 512 a characteristic of each detected acoustic signal may be determined. Characteristics of the detected acoustic signal may be acoustic travel time and acoustic amplitude.

In Step 514 a density profile may be determined at an instant in time coinciding with an arrival time of each detected acoustic signal used to determine the characteristic. If a cement bond failure based on a displacement of the inner cylinder (206) is not observed at a decision node (516) the method recycles back to Step 506 and repeats. If the cement bond failure is observed at the decision node (516) the method proceeds to the next step. In this manner a plurality of density profiles may be created.

In Step 518 each of the density profiles created through iterations of Step 506 thru Step 514 may be compiled to create a 4D settling density profile. The settling density profile may be used to assess the settling characteristics of the test cement. In some embodiments, a shear bond strength can also be determined in Step 518 using a similar calculation method described above with respect to Step 418 of FIG. 4.

In some embodiments, a settling density profile can be generated without testing the shear bond strength at the same time. In such embodiments, the stress applied in Step 504 may not include the axial stress (304) and Step 516 may be omitted. That is, the cement column is not subjected to the axial stress (304) to observe cement bond failure or cement displacement. Consequently, iterations of Step 506 thru Step 514 are not performed. In these embodiments, the period of time over which the plurality of acoustic signals are emitted and detected (Steps 508 and 510) may include the cement curing time.

The acoustically based determination of the settling density profile may provide a more complete description of the settling characteristics as the density profile can be determined at any interval of time over the entirety of cement curing process which cannot be done in the typical destructive process which requires the cement to be cured (hardened) at least to some degree. A better understanding of the settling density profile may lead to more reliable cement mixture for use in a wellbore environment (100).

Figure 6:
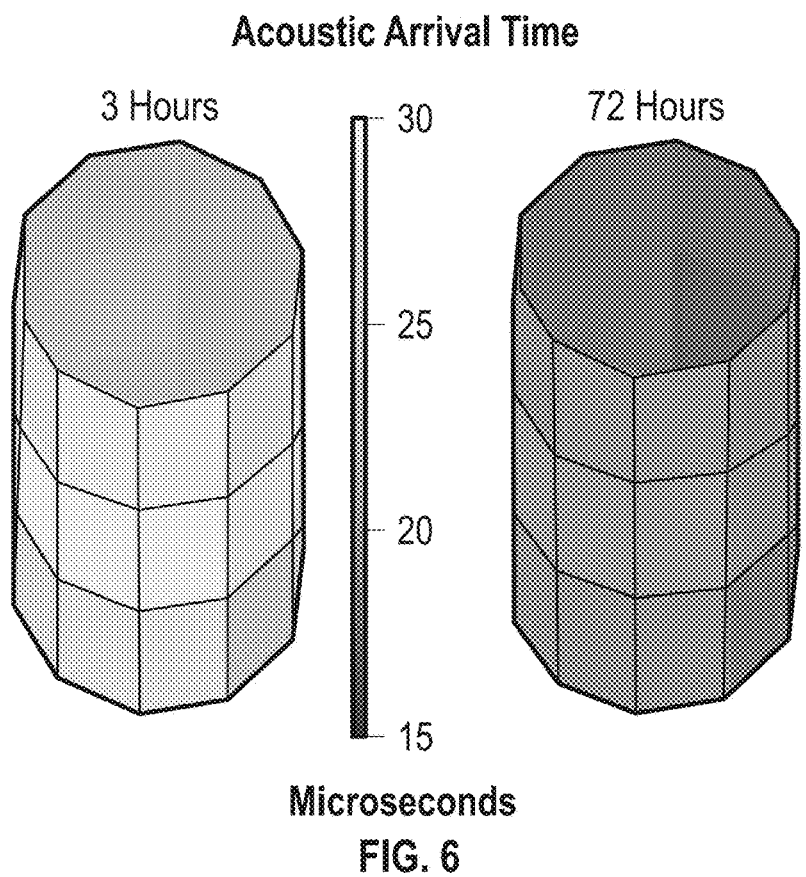
FIG. 6 shows two time-lapse images of the acoustic arrival time in a cement column in accordance with one or more embodiments.

Two example (3D) profiles are shown in FIG. 6. FIG. 6 shows two time-lapse images of the acoustic arrival time in a cement column in the annulus (208). Images like those shown in FIG. 6 may be used to create a plurality of density profiles for the test cement as decrease of acoustic arrival time is analogous to increase of cement strength or density. Further, the density profile may be compiled to produce a settling density profile over time (4D profile). On the one hand, the image taken at 3 hours may indicate a greater acoustic arrival time at a given point along the length of the cement column (e.g., top, middle, or bottom), and hence a lower acoustic velocity, than the image taken at 72 hours. The decreased acoustic arrival time, and hence greater acoustic velocity, may correspond to the cement curing process as the acoustic waves travel faster in solid cement compared to semisolid cement.

On the other hand, as shown in each of the two images in FIG. 6, the acoustic arrival time varies little from the top to the bottom of the cement column. This indicates that no outstanding settling issues exist during the curing process of the cement. One of ordinary skill in the art will appreciate that, if settling is outstanding in the tested cement, acoustic arrival time profiles such as the 3D profiles shown in FIG.

6 will exhibit an ever-increasing divergence of acoustic arrival times from the top to the bottom of the cement column at any given time over the cement curing process. The dispersion of the acoustic arrival times from the top to the bottom of the cement column may become permanent near the end of the curing process, that is, when settling substantially stops. A 4D profile composed of a plurality of such 3D profiles may present an animation of the change of the dispersion of the acoustic arrival times from the top to the bottom of the cement column. 3D and 4D density profiles created based on the acoustic arrival time profiles may follow a reverse pattern. One of ordinary skill in the art will appreciate that a density profile created based on acoustic amplitude profiles is also possible as increase of acoustic amplitude is analogous to increase of cement strength or density. In this case, the density profile and the acoustic amplitude profile may follow the same pattern.

The 3D and 4D density profiles thus created allow visual observance of possible settling of a tested cement at any given time and the evolution of the settling over the cement curing process. Furthermore, the density profiles may be used to locate weak points in the cement that may lead to failure.

Figure 7:
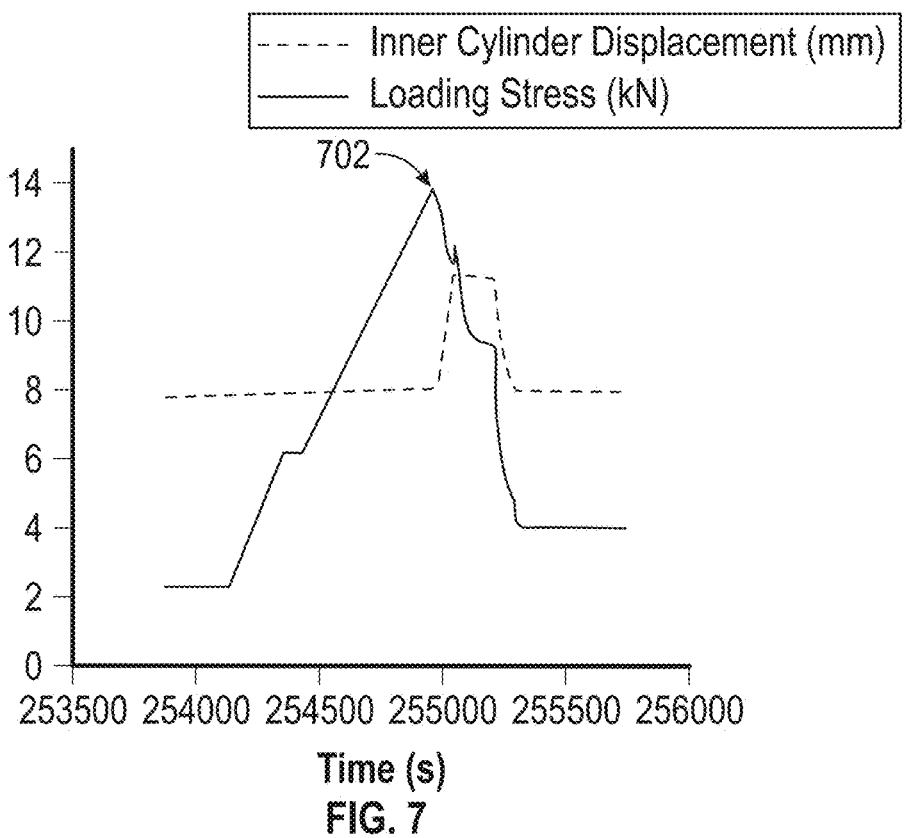
FIG. 7 shows a chart in accordance with one or more embodiments.

FIG. 7 shows a chart in accordance with one or more embodiments. The chart in FIG. 7 shows an axial displacement of the inner cylinder and the loading stress applied by the loading piston (322). The peak load (702) occurs when the displacement rapidly increases as the load applied rapidly decreases from the maximum load stress value.

FIGS. 8A-8D show example relationships between acoustic characteristics, time, and stress applied by the testing system (300). A calibrated relationship between a curing effect of the test cement and the characteristic may be determined subject to different test parameters, such as the horizontal stress (310), the radial stress (316), and the temperature.

Figure 8B:
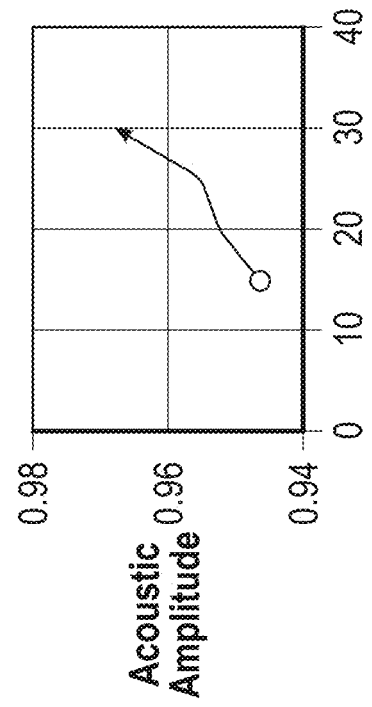
FIG. 8B shows a relationship in accordance with one or more embodiments.
Figure 8D:
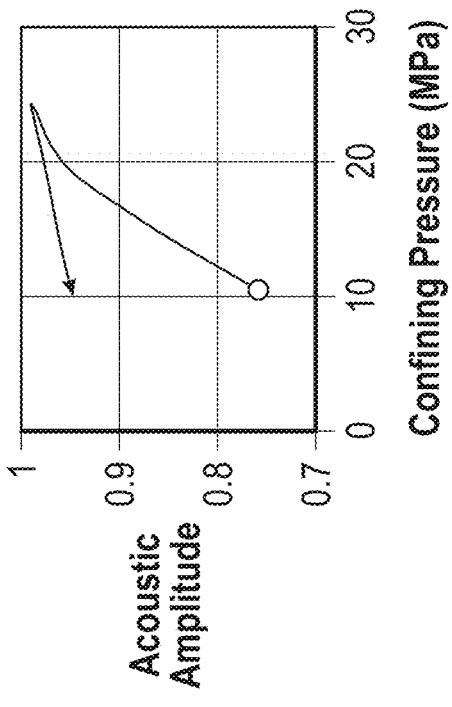
FIG. 8D shows a relationship in accordance with one or more embodiments.
Figure 8A:
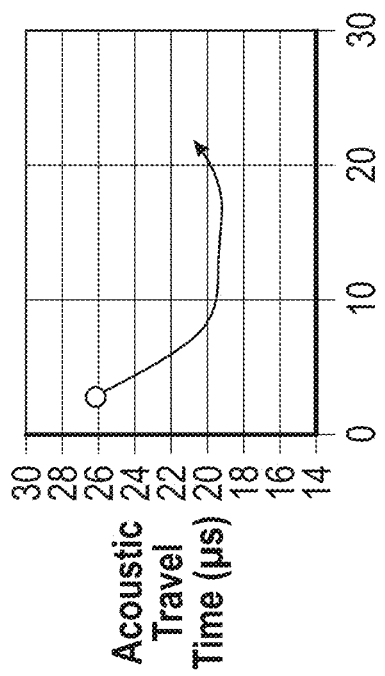
FIG. 8A shows a relationship in accordance with one or more embodiments.

FIG. 8A shows a cement curing effect on acoustic travel time. In this example, the travel time reduces, i.e., the acoustic waves travel faster as the test cement cures, which may correspond to increasing cement strength.

FIG. 8B shows the effect of a casing pressure, i.e., the radial stress (316) in the inner cylinder (206), on the acoustic amplitude. In this example, the acoustic amplitude increases with increasing casing pressure. The increasing casing pressure may correspond to increasing pressure on the cement in the annulus (208) which may compact the cement and may correspond to increasing cement strength. The increasing cement strength may be related to the closure of micropores or fractures in the cement.

Figure 8C:
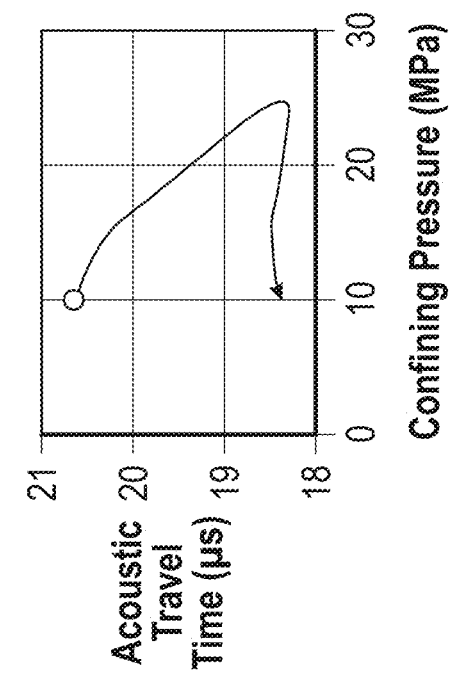
FIG. 8C shows a relationship in accordance with one or more embodiments.

FIG. 8C shows the effect of a confining pressure, i.e., the horizontal stress (310), on the acoustic travel time. In this example, the acoustic travel time decreases with increasing confining pressure. The reduction in travel time may correspond to the closure of micropores or fractures and may be interpreted as increasing cement strength. In this example, the confining pressure is decreased again to the original level after being increased to a certain level. The travel time becomes stable when the confining pressure is no longer increased or is decreased as shown because the cement has become more compact due to the previously increased confining pressure.

FIG. 8D shows the effect of the confining pressure on the acoustic amplitude. In this example, the acoustic amplitude increases with increasing confining pressure. The increasing amplitudes may correspond to the closure of micropores or fractures and may be interpreted as increasing cement strength. A similar stabilization of the acoustic amplitude when the confining pressure is decreased to the original level is observed.

A computer may be used to transmit activation signals to the acoustic transmitter (250) to initiate the emission of the acoustic signals. Similarly, a computer may receive recordings of the acoustic signals detected by the acoustic receiver (258). Further, the computer may synchronize the emission and detection of acoustic signals to facilitate the measurement of acoustic travel times with high precision. A computer may also be used to detect an arrival time from a recorded acoustic signal waveform. In addition to controlling the acoustic transmitter (250) and recording acoustic signal detected by the acoustic receiver (258) the computer may be configured to determine characteristics of each of the acoustic signals.

Figure 9:
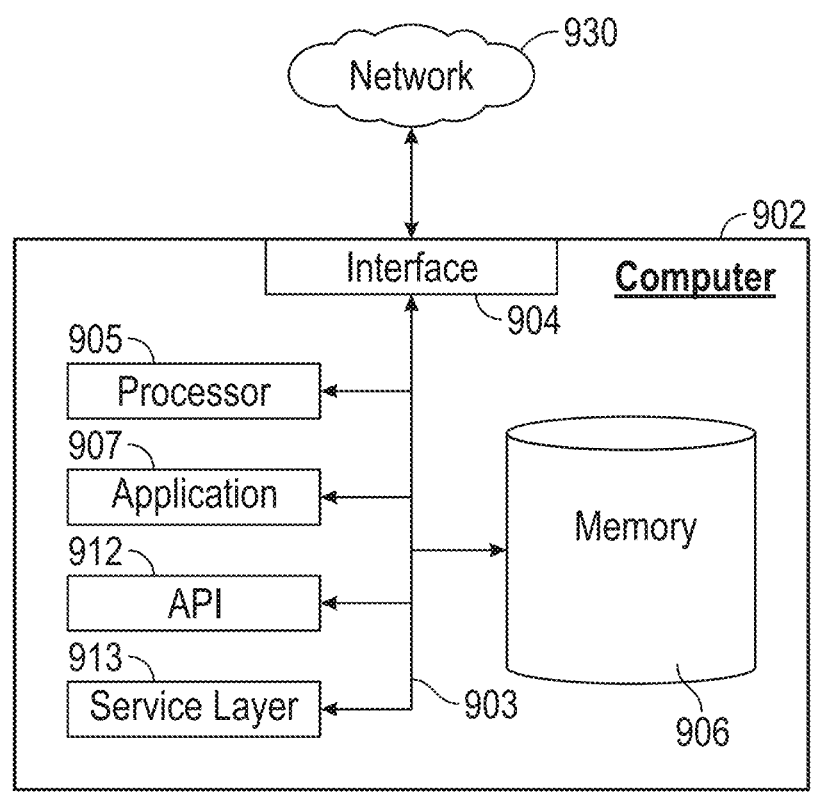
FIG. 9 depicts a computer in accordance with one or more embodiments.

FIG. 9 depicts a block diagram of the computer (902) used to provide computational functionalities associated with described algorithms, methods, functions, processes, flows, and procedures as described in this disclosure, according to one or more embodiments. The computer (902) illustration is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (902) may include a computer that includes an input device, such as a keypad, keyboard, touch screen, or other device that can accept user information, and an output device that conveys information associated with the operation of the computer (902), including digital data, visual, or audio information (or a combination of information), or a Graphical User Interface (GUI).

The computer (902) can serve in a role as a client, network component, a server, a database or other persistency, or any other component (or a combination of roles) of a computer system for performing the subject matter described in the instant disclosure. The illustrated computer (902) is communicably coupled with a network (930). In some implementations, one or more components of the computer (902) may be configured to operate within environments, including cloud-computing-based, local, global, or other environment (or a combination of environments).

At a high level, the computer (902) is an electronic computing device operable to receive, transmit, process, store, or manage data and information associated with the described subject matter. According to some implementations, the computer (902) may also include or be communicably coupled with an application server, e-mail server, web server, caching server, streaming data server, business intelligence (BI) server, or other server (or a combination of servers).

The computer (902) can receive requests over network (930) from a client application (for example, executing on another computer (902)) and responding to the received requests by processing the requests in an appropriate software application. In addition, requests may also be sent to the computer (902) from internal users (for example, from a command console or by other appropriate access method), external or third-parties, other automated applications, as well as any other appropriate entities, individuals, systems, or computers.

Each of the components of the computer (902) can communicate using a system bus (903). In some implementations, any or all of the components of the computer (902), both hardware or software (or a combination of hardware and software), may interface with each other or the interface (904) (or a combination of both) over the system bus (903) using an application programming interface (API) (912) or a service layer (913) (or a combination of the API (912) and service layer (913). The API (912) may include specifications for routines, data structures, and object classes. The API (912) may be either computer-language independent or dependent and refer to a complete interface, a single function, or even a set of APIs. The service layer (913) provides software services to the computer (902) or other components (whether or not illustrated) that are communicably coupled to the computer (902). The functionality of the computer (902) may be accessible for all service consumers using this service layer. Software services, such as those provided by the service layer (913), provide reusable, defined business functionalities through a defined interface. For example, the interface may be software written in JAVA, C++, or other suitable language providing data in extensible markup language (XML) format or another suitable format. While illustrated as an integrated component of the computer (902), alternative implementations may illustrate the API (912) or the service layer (913) as stand-alone components in relation to other components of the computer (902) or other components (whether or not illustrated) that are communicably coupled to the computer (902). Moreover, any or all parts of the API (912) or the service layer (913) may be implemented as child or sub-modules of another software module, enterprise application, or hardware module without departing from the scope of this disclosure.

The computer (902) includes an interface (904). Although illustrated as a single interface (904) in FIG. 9, two or more interfaces (904) may be used according to particular needs, desires, or particular implementations of the computer (902). The interface (904) is used by the computer (902) for communicating with other systems in a distributed environment that are connected to the network (930). Generally, the interface (904) includes logic encoded in software or hardware (or a combination of software and hardware) and operable to communicate with the network (930). More specifically, the interface (904) may include software supporting one or more communication protocols associated with communications such that the network (930) or interface's hardware is operable to communicate physical signals within and outside of the illustrated computer (902).

The computer (902) includes at least one computer processor (905). Although illustrated as a single computer processor (905) in FIG. 9, two or more processors may be used according to particular needs, desires, or particular implementations of the computer (902). Generally, the computer processor (905) executes instructions and manipulates data to perform the operations of the computer (902) and any algorithms, methods, functions, processes, flows, and procedures as described in the instant disclosure.

The computer (902) also includes a memory (906) that holds data for the computer (902) or other components (or a combination of both) that can be connected to the network (930). For example, memory (906) can be a database storing data consistent with this disclosure. Although illustrated as a single memory (906) in FIG. 9, two or more memories may be used according to particular needs, desires, or particular implementations of the computer (902) and the described functionality. While memory (906) is illustrated as an integral component of the computer (902), in alternative implementations, memory (906) can be external to the computer (902).

The application (907) is an algorithmic software engine providing functionality according to particular needs, desires, or particular implementations of the computer (902), particularly with respect to functionality described in this disclosure. For example, application (907) can serve as one or more components, modules, applications, etc. Further, although illustrated as a single application (907), the application (907) may be implemented as multiple applications (907) on the computer (902). In addition, although illustrated as integral to the computer (902), in alternative implementations, the application (907) can be external to the computer (902).

There may be any number of computers (902) associated with, or external to, a computer system containing computer (902), wherein each computer (902) communicates over network (930). Further, the term "client," "user," and other appropriate terminology may be used interchangeably as appropriate without departing from the scope of this disclosure. Moreover, this disclosure contemplates that many users may use one computer (902), or that one user may use multiple computers (902).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A cement bond test cell for use in a test chamber, comprising:
    an outer cylinder;
    an inner cylinder coaxially disposed within the outer cylinder along a central axis, wherein the inner cylinder defines an inner volume configured to be filled with a fluid, and wherein an annulus is formed between the outer cylinder and the inner cylinder and configured to be filled with a test cement;
    an acoustic transmitter disposed within the inner volume and configured to be acoustically coupled to an interior surface of the inner cylinder by the fluid; and
    at least one acoustic receiver acoustically coupled to an exterior surface of the outer cylinder.

2. The cement bond test cell of claim 1, further comprising an electrical feedthrough that connects the acoustic transmitter to an activation device disposed outside of the cement bond test cell.

3. The cement bond test cell of claim 1, further comprising an acoustic support structure coaxially disposed within the inner cylinder.

4. The cement bond test cell of claim 1, further comprising a test cement channel that connects the annulus to a test cement reservoir through a test cement pump.

5. The cement bond test cell of claim 1, wherein the acoustic transmitter comprises a plurality of acoustic sources, wherein each of the acoustic sources is affixed at an axial elevation along the central axis inside of the inner cylinder, and wherein each of the acoustic sources is a piezoelectric crystal.

6. The cement bond test cell of claim 1, wherein the at least one acoustic receiver comprises a plurality of acoustic detectors, wherein the plurality of acoustic detectors form a coplanar acoustic detector array, wherein each acoustic detector is disposed at an azimuthal interval around a circumference of the outer cylinder, and wherein the coplanar acoustic detector array is placed at an elevation coincident with an axial elevation of the acoustic transmitter.

7. The cement bond test cell of claim 1, further comprising a fluid pressure channel, wherein the fluid is configured to be pressurized through the fluid pressure channel.

8. A method, comprising:
installing a cement bond test cell into a test chamber configured to apply a stress in the cement bond test cell;
filling an annulus between an outer cylinder and an inner cylinder of the cement bond test cell with a test cement;
applying a stress to the cement bond test cell;
emitting a plurality of acoustic signals from an acoustic transmitter disposed in a fluid filling the inner cylinder over a period of time;
detecting each acoustic signal using an acoustic receiver acoustically coupled to an exterior surface of the outer cylinder over the period of time;
determining a characteristic of each detected acoustic signal;
detecting a commencement of a cement bond failure based, at least in part, on the characteristic of each of the detected acoustic signals; and
determining a shear bond strength based, at least in part, on a measured axial stress at the commencement of the cement bond failure.

9. The method of claim 8, wherein the characteristic is an acoustic travel time or an acoustic amplitude.

10. The method of claim 8, wherein the period of time is a duration of time that coincides with a curing of the cement and the commencement of the cement bond failure.

11. The method of claim 8, further comprising determining a calibrated relationship between a curing effect of the test cement and the characteristic.

12. The method of claim 8, further comprising:
selecting a composition of a cement based, at least in part, on the shear bond strength of the test cement;
mixing the cement; and
pumping the cement into an annular space between a casing and a wellbore.

13. A method, comprising:
installing a cement bond test cell into a test chamber configured to apply a stress in the cement bond test cell;
filling an annulus between an outer cylinder and an inner cylinder of the cement bond test cell with a test cement;
applying a stress to the cement bond test cell;
emitting a plurality of acoustic signals from an acoustic transmitter disposed in a fluid filling the inner cylinder over a period of time;
detecting each acoustic signal using an acoustic receiver acoustically coupled to an exterior surface of the outer cylinder over the period of time;
determining a characteristic of each detected acoustic signal; and
determining a density profile of the test cement at an instant in time based, at least in part, on the characteristic.

14. The method of claim 13, further comprising compiling a 4D settling density profile based on a plurality of density profiles determined at a plurality of instants in time.

15. The method of claim 13, wherein the characteristic is an acoustic travel time or an acoustic amplitude.

16. The method of claim 13, wherein the period of time is a duration of time that coincides with a curing of the cement.

17. The method of claim 13, further comprising determining a calibrated relationship between a curing effect of the test cement and the characteristic.

18. The method of claim 13, further comprising:
selecting a composition of a cement based, at least in part, on the settling density profile of the test cement;
mixing the cement; and
pumping the cement into an annular space between a casing and a wellbore.

19. A system, comprising:
a testing system comprising a test chamber configured to apply a stress in the test chamber;
a cement bond test cell configured to be installed in the test chamber, wherein the testing system is configured to apply a stress to the cement bond test cell, and wherein the cement bond test cell comprises:
an outer cylinder,
an inner cylinder coaxially disposed within the outer cylinder, wherein the inner cylinder defines an inner volume configured to be filled with a fluid, and wherein an annulus is formed between the outer cylinder and the inner cylinder and configured to be filled with a cement,
an acoustic transmitter disposed within the inner volume of the inner cylinder and configured to be acoustically coupled to an interior surface of the inner cylinder by the fluid, and
an acoustic receiver acoustically coupled to an exterior surface of the outer cylinder; and
a computer processor configured to:
control the stress applied by the testing system in the test chamber,
activate the acoustic transmitter over a period of time,
record an acoustic signal detected by the acoustic receiver over the period of time,
determine a characteristic of the acoustic signal,
determine a density profile of the test cement at an instant in time based, at least in part, on the characteristic,
detect a commencement of a cement bond failure based, at least in part, on the characteristic of the acoustic signal detected by the acoustic receiver, and
determine a shear bond strength based, at least in part, on a measured axial stress at the commencement of the cement bond failure.

20. The system according to claim 19, further comprising:
a cement mixing system to mix a cement based, at least in part, on one of the shear bond strength or the density profile; and
a cement pumping system to pump the cement into an annulus between an exterior surface of a casing and a wellbore.

* * * * *